US009661856B1

(12) United States Patent
Bright et al.

(10) Patent No.: US 9,661,856 B1
(45) Date of Patent: May 30, 2017

(54) SYNERGY OF PLANT ANTIMICROBIALS WITH SILVER

(71) Applicant: The Arizona Board of Regents on behalf of the University of Arizona, Tucson, AZ (US)

(72) Inventors: Kelly R. Bright, Tucson, AZ (US); Sadhana Ravishankar, Tucson, AZ (US); Damian H. Gilling, Tampa, FL (US)

(73) Assignee: The Arizona Board of Regents on Behalf of The University of Arizona, Tucson, AZ (US)

( * ) Notice: Subject to any disclaimer, the term of this patent is extended or adjusted under 35 U.S.C. 154(b) by 429 days.

(21) Appl. No.: 14/010,257

(22) Filed: Aug. 26, 2013

Related U.S. Application Data

(60) Provisional application No. 61/743,048, filed on Aug. 24, 2012.

(51) Int. Cl.
| | | |
|---|---|---|
| A01N 25/08 | (2006.01) | |
| A01N 31/08 | (2006.01) | |
| A01N 35/02 | (2006.01) | |
| A01N 59/16 | (2006.01) | |
| A01N 65/28 | (2009.01) | |

(52) U.S. Cl.
CPC ............. *A01N 59/16* (2013.01); *A01N 25/08* (2013.01); *A01N 31/08* (2013.01); *A01N 35/02* (2013.01); *A01N 65/28* (2013.01)

(58) Field of Classification Search
CPC ........ A01N 25/08; A01N 31/08; A01N 35/02; A01N 59/16; A01N 65/28
See application file for complete search history.

(56) References Cited

U.S. PATENT DOCUMENTS

| 7,989,043 B2 | 8/2011 | Salemi | |
|---|---|---|---|
| 7,998,498 B2 | 8/2011 | Szycher | |
| 2006/0219641 A1* | 10/2006 | Kepner | .................. A01N 25/12 210/723 |

FOREIGN PATENT DOCUMENTS

| WO | WO 2008/144014 A2 | 11/2008 | |
|---|---|---|---|
| WO | WO 2011/002929 A1 | 1/2011 | |
| WO | WO 2011002929 A1 * | 1/2011 | ............. A01N 31/02 |

OTHER PUBLICATIONS

Adams et al., "Factors Affecting the Efficacy of Washing Procedures Used in the Production of Prepared Salads," *Food Microbiol.* 6:69-77, 1989.
Beuchat et al., "Development of a Proposed Standard Method for Assessing the Efficacy of Fresh Produce Sanitizers," *J Food Protect.* 64:1103-1109, 2001.
Castillo and Rodriguez-García, "Bacterial Hazards in Fresh and Fresh-Cut Produce: Sources and Control," in Preharvest and Postharvest Food Safety, Beier RC, Pillai SD, Phillips DT, Riprin RL (Eds.), pp. 43-57, Black Publishing Ames, IA. 2004.
Doyle, "Food Antimicrobials, Cleaners, and Sanitizers," *Food Research Institute*, UW-Madison, FRI Briefings 9:1-15, 2005.
Konwarh et al., "Biomimetic Preparation of Polymer-Supported Free Radical Scavenging, Cytocompatible and Antimicrobial 'Green' Silver Nanoparticles Using Aqueous Extract of *Citrus sinensis* Peel," *Colloids Surf B Biointerfaces* 84:338-345, 2011.
Koseki et al., "Influence of Inoculation Method, Spot Inoculation Site, and Inoculation Size on the Efficacy of Acidic Electrolyzed Water Against Pathogens on Lettuce," *J Food Prot.* 66:2010-2016, 2003.
Koseki et al., "Efficacy of Acidic Electrolyzed Water for Microbial Decontamination of Cucumbers and Strawberries," *J Food Prot.* 67:1247-1251, 2004.
Li et al., "Use of Natural Antimicrobials From a Food Safety Perspective for Control of *Staphylococcus aureus*," *Curr Pharm Biotechnol.* 12:1240-1254, 2011.
Pirovani et al., "Reduction of Chlorine Concentration and Microbial Load During Washing-Disinfection of Shredded Lettuce," *Int J Food Sci Tech.* 39:341-347, 2004.
Rodgers et al., "A Comparison of Different Chemical Sanitizers for Inactivating *Escherichia coli* O157:H7 and *Listeria monocytogenes* in Solution and on Apples, Lettuce, Strawberries, and Cantaloupe," *J Food Prot.* 67:721-731, 2004.
Sapers, "Disinfection of Contaminated Produce with Conventional Washing and Sanitizing Technology," in The Produce Contamination Problem: Causes and Solution, Sapers GM, Solomon EB, Matthews KR (Eds.), pp. 393-424, Academic Press, Boston, Massachusetts, 2009.
Seo and Frank, "Attachment of *Escherichia coli* O157:H7 to Lettuce Leaf Surface and Bacterial Viability in Response to Chlorine Treatment as Demonstrated by Using Confocal Scanning Laser Microscopy," *J Food Prot.* 62:3-9, 1999.
Ukuku and Sapers, "Microbiological Safety Issues of Fresh Melons," pp. 231-251, in Microbiology of Fruits and Vegetables, Sapers GM, Gorny JR, Yousef AE (Eds.), CRC Press, Boca Raton, Florida, 2005.
Yuk et al., "The Effectiveness of Sanitizer Treatments in Inactivation of *Salmonella* spp. from Bell Pepper, Cucumber, and Strawberry," *J Food Sci.* 71:95-99, 2006.
Adams et al., "The FEMA GRAS Assessment of Cinnamyl Derivatives Used as Flavor Ingredients," *Food Chem Toxicol* 42:157-185, 2004.
Anonymous in *Hach Water Analysis Handbook*, pp. 555-558, Loveland: Hach Company, 1989.

(Continued)

*Primary Examiner* — Michael B Pallay
(74) *Attorney, Agent, or Firm* — Klarquist Sparkman, LLP

(57) ABSTRACT

Citral, cinnamaldehyde, carvacrol, and allspice oil were found to be highly effective antimicrobials, producing statistically significant reductions in *Escherichia coli* populations within minutes. In addition, synergy was observed between silver ions and these essential oils, thereby lessening the amount of the plant antimicrobial required to produce the same effect. Based on these observations, compositions including these agents and there use as an antimicrobial treatment that is safe for human consumption, are active in the presence of organic matter, are provided.

20 Claims, No Drawings

(56) References Cited

OTHER PUBLICATIONS

Armon et al., "Controlling Biofilm Formation by Hydrogen Peroxide and Silver Combined Disinfectant," *Water Sci Technol*. 42:187-192, 2000.
Beuchat, L.R., "Surface Decontamination of Fruits and Vegetables Eaten Raw: A Review," *Food Saf. Issues*, WHO/FSF/FOS/ 98.2. World Health Organization, Geneva.
Burt, S., "Essential Oils: Their Antibacterial Properties and Potential Applications in Foods—A Review," *Int J Food Microbiol*. 94:223-253, 2004.
Butkus et al., "Use of Aqueous Silver to Enhance Inactivation of Coliphage MS-2 by UV Disinfection," *Appl Environ Microbiol*. 70:2848-2853, 2004.
Callaway et al., "Citrus Products Decrease Growth of *E. coli* O157:H7 and *Salmonella typhimurium* in Pure Culture and in Fermentation with Mixed Ruminal Microorganisms *In Vitro*," *Foodborne Pathog Dis*. 5:621-627, 2008.
Chang et al., "The Interaction of Aqueous Solutions of Chlorine with Malic Acid, Tartaric Acid, and Various Fruit Juices, a Source of Mutagens," *Anal Lett*. 21:2049-2067, 1988.
Cox and Markham, "Susceptibility and Intrinsic Tolerance of *Pseudomonas aeruginosa* to Selected Plant Volatile Compounds," *J Appl Microbiol*. 103:930-936, 2007.
Deupree et al., "Synergy of Nitric Oxide and Silver Sulfadiazine Against Gram-Negative, Gram-Positive, and Antibiotic-Resistant Pathogens," *Mol Pharm*. 7:2289-2296, 2010.
Didry et al., "Activity of Thymol, Carvacrol, Cinnamaldehyde and Eugenol on Oral Bacteria," *Pharm Acta Helv*. 69:25-28, 1994.
Dillon, VM, "Natural Anti-Microbial Systems (a) Preservative Effects During Storage," in Encyclopedia of Food Microbiology, pp. 1570-1576, Robinson RK, Batt CA, Patel P (Eds.), Academic Press, Boston, Massachussetts, 1999.
Environmental Protection Agency, "National Secondary Drinking Water Regulations," http://www.epa.gov/safewater/mcl.html. Retrived Jul. 20, 2011.
Friedman et al., "Bactericidal Activities of Plant Essential Oils and Some of Their Isolated Constituents Against *Campylobacter jejuni*, *Escherichia coli*, *Listeria monocytogenes*, and *Salmonella enterica*," *J Food Prot*. 65:1545-1560, 2002.
Gentry and Cope, "Using Silver to Reduce Catheter-Associated Urinary Tract Infections," *Nurs Stand* 19:51-54, 2005.
Gupta and Ravishankar, "A Comparison of the Antimicrobial Activity of Garlic, Ginger, Carrot, and Turmeric Pastes against *Escherichia coli* O157:H7 in Laboratory Buffer and Ground Beef," *Foodborne Pathog Dis*. 2:330-340, 2005.
Hidaka et al., "Disappearance of Residual Chlorine and Formation of Chloroform in Vegetables Treated with Sodium Hyphochlorite," *J Food Hyg Soc Japan* 33:267-273, 1992. (Includes English Abstract.).
Ibarluzea et al., "Determinants of the Microbiological Water Quality of Indoor Swimming-Pools in Relation to Disinfection," *Water Res*. 32:865-871, 1998.
Kim et al., "Formation of Disinfection By-Products in Chlorinated Swimming Pool Water," *Chemosphere* 46:123-130, 2002.
Knowles et al., "Antimicrobial Action of Carvacrol at Different Stages of Dual-Species Biofilm Development by *Staphylococcus aureus* and *Salmonella enterica* Serovar Typhimurium," *Appl Environ Microbiol*. 71:797-803, 2005.
Kurek et al., "New Antibacterial Therapeutics and Strategies," *Pol J Microbiol*. 60:3-12, 2011.
Lansdown, "Silver in Health Care: Antimicrobial Effects and Safety in Use," *Curr Probl Dermatol* 33:17-34, 2006.
Matthews, K.R. Leafy Vegetables, in *The Produce Contamination Problem: Causes and Solutions* ed. Sapers, G.M., Solomon, E.B. and Matthews, K.R. pp. 165-188. Boston: Academic Press, 2009.
Mihara and Shibamoto, "Photochemical Reactions of Eugenol and Related Compounds: Synthesis of New Flavor Chemicals," *J. Agric Food Chem* 30:1215-1218, 1982.
Nannapaneni et al., "Antimicrobial Activity of Commercial Citrus-Based Natural Extracts Against *Escherichia coli* O157:H7 Isolates and Mutant Strains," *Foodborne Pathog Dis*. 5:695-699, 2008.
Ogata et al., "Antioxidant Activity of Eugenol and Related Monomeric and Dimeric Compounds," *Chem Pharm Bull (Tokyo)* 48:1467-1469, 2000.
Olasupo et al., "Activity of Natural Antimicrobial Compounds Against *Escherichia coli* and *Salmonella enterica* Serovar Typhimurium," *Lett Appl Microbiol*. 36:448-451, 2003.
Penalver et al., "Antimicrobial Activity of Five Essential Oils Against Origin Strains of the Enterobacteriaceae Family," *APMIS* 113:1-6, 2005.
Ravishankar et al., "Plant-Derived Compounds Inactivate Antibiotic-Resistant *Campylobacter jejuni* Strains," *J Food Prot*. 71:1145-1149, 2008.
Ravishankar et al., "Edible Apple Film Wraps Containing Plant Antimicrobials Inactivate Foodborne Pathogens on Meat and Poultry Products," *J Food Sci*. 74:M440-M445, 2009.
Ravishankar et al., "Carvacrol and Cinnamaldehyde Inactivate Antibiotic-Resistant *Salmonella enterica* in Buffer and on Celery and Oysters," *J Food Prot*. 73:234-240, 2010.
Ress et al., "Toxicology and Carcinogenesis Studies of Microencapsulated Citral in Rats and Mice," *Toxicol Rep*. 71:198-206, 2003.
Silver, S., "Bacterial Silver Resistance: Molecular Biology and Uses and Misuses of Silver Compounds," *FEMS Microbiol Rev*. 27:341-353, 2003.
Silvestry-Rodriguez et al., "Inactivation of *Pseudomonas aeruginosa* and *Aeromonas hydrophila* by Silver in Tap Water," *J Environ Sci Health, Part A Tox Hazard Subst Environ Eng* 42:1579-1584, 2007.
Silvestry-Rodriguez, N., "Silver as a Disinfectant," *Rev Environ Contam Toxicol*. 191:23-45, 2007.
Singh et al., "Sequential Disinfection of *Escherichia coli* O157:H7 Inoculated Alfalfa Seeds Before and During Sprouting Using Aqueous Chlorine Dioxide, Ozonated Water, and Thyme Essential Oil," *Lebensm Wiss U.-Technol*. 36:235-243, 2003.
Somolinos et al., "Inactivation of *Escherichia coli* by Citral ," *J Appl Microbiol*. 108:1928-1939, 2009.
Suslow, T., "Chapter 6. Chlorination in the Production and Postharvest Handling of Fresh Fruits and Vegetables," In Fruit and Vegetable Processing, McLaren D (Ed.), Accessed Nov. 22, 2013, http://www.siphidaho.org/env/pdf/Chlorination_of_fruits_and_veggies.PDF.
Uhart et al., "Effect of Spices on Growth and Survival of *Salmonella Typhimurium* DT 104 in Ground Beef Stored at 4 and 8° C.," *J Food Saf*. 26:115-125, 2006.
Yahya et al., "Inactivation of Coliphage MS-2 and Poliovirus by Copper, Silver and Chlorine," *Can J Microbiol*. 38:430-435, 1992.

\* cited by examiner

SYNERGY OF PLANT ANTIMICROBIALS WITH SILVER

CROSS REFERENCE TO RELATED APPLICATION

This application claims priority to U.S. Provisional Application No. 61/743,048 filed Aug. 24, 2012, herein incorporated by reference.

ACKNOWLEDGMENT OF GOVERNMENT SUPPORT

This invention was made with government support under Grant No. 2010-51300-21760 awarded by the USDA/NIFA. The government has certain rights in the invention.

FIELD

This application provides antimicrobial compositions that include one or more of citral, cinnamaldehyde, carvacrol, and allspice in combination with silver ions. Also provided are methods of using the antimicrobial compositions, for example to kill or reduce the number of microorganisms.

BACKGROUND

There will always be a need for new effective alternatives to existing sanitizers and disinfectants as new pathogens emerge and microorganisms develop resistances to existing antimicrobials. In addition, in certain applications, only "green" or non-toxic antimicrobials are desired: for instance, to sanitize food or food contact surfaces, to treat water, or to disinfect environmental surfaces in areas with sensitive populations (e.g., day care centers, hospital intensive care units) that may not be able to tolerate exposure to harsher chemicals. Also, in some current applications, existing antimicrobials have limited efficacy such as in situations in which the antimicrobial is exposed to high levels of organic material.

Natural antimicrobials from plants are one such possible alternative. Plants produce antimicrobials in various areas such as in the roots, leaves, bark, and stem, coinciding with the various assaults that the plant might encounter in the environment (Burt 2004). Numerous plant extracts, essential oils, and their components have significant antimicrobial properties (Didry et al., 1994; Friedman et al., 2002; Olasupo et al., 2003; Singh et al., 2003; Gupta and Ravishankar 2005; Knowles et al., 2005; Peñalver et al. 2005; Uhart et al., 2006; Callaway et al., 2008; Nannapaneni et al., 2008; Ravishankar et al., 2008; Ravishankar et al., 2009; Ravishankar et al., 2010). Many plant antimicrobials are used and are often found in the average household kitchen cabinet. Such common and longstanding usage has earned these antimicrobials the label of Generally Regarded As Safe (GRAS) compounds (Dillon 1999; Ress et al., 2003; Adams et al., 2004; Knowles et al., 2005). In addition, these compounds are likely not affected by the presence of organics and therefore may be easier to maintain at the appropriate effective concentrations than antimicrobials such as chlorine (Dillon 1999; Silvestry-Rodriguez et al., 2007a; Matthews 2009).

SUMMARY

Plant antimicrobials, namely citral, cinnamaldehyde, carvacrol, and allspice (such as eugenol), in combination with silver ions, are shown herein to have an enhanced or synergistic antimicrobial efficacy against *Escherichia coli*. Based on these observations, provided herein are antimicrobial compositions that include one or more of citral, cinnamaldehyde, carvacrol, and allspice (e.g., eugenol), in combination with silver ions, as well as methods of using such combinations.

Thus, provided herein are antimicrobial compositions that include one of more of citral, cinnamaldehyde, carvacrol, and allspice (e.g., eugenol), in combination with silver ions. In some examples the composition also includes water and/or ethanol. Such a composition can be in a liquid form, such as a spray, or can be present on a solid support, such as a layer of absorbent/adsorbent material.

The disclosure also provides methods of killing microorganisms, such as bacteria, bacterial and fungal spores, or viruses, by applying or contacting the antimicrobial compositions disclosed herein to the microorganism. Such methods can be used to decontaminate items and solid surfaces, such as produce and meats, as well as work surfaces and other areas that may contain undesirable microorganisms.

The foregoing and other objects and features of the disclosure will become more apparent from the following detailed description.

DETAILED DESCRIPTION

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references.

All publications, patent applications, patents, and other references mentioned herein are incorporated by reference in their entirety for all purposes.

In order to facilitate review of the various embodiments of the disclosure, the following explanations of specific terms are provided:

Bacteria: Any of various prokaryotic organisms, including organisms within various phyla in the Kingdom Procaryotae. The terms encompass all microorganisms commonly regarded as bacteria, including *Mycoplasma, Chlamydia, Actinomyces, Streptomyces*, and *Rickettsia*. The term also includes cocci, bacilli, spirochetes, spheroplasts, protoplasts, and so forth.

Decontamination: To substantially inactivate or remove unwanted microorganisms or bacterial or fungal spores, for example by killing a substantial number of microorganisms present. In some examples, decontamination with the disclosed antimicrobial compositions kills at least 90%, at least 95%, at least 99%, at least 99.9%, at least 99.99%, or at least 99.999% of microorganisms present following contact with the composition. For example, decontamination with the disclosed antimicrobial compositions reduces the number of microorganisms (such as bacteria) present by at least 1-log, at least 2-logs, at least 3-logs, or at least 5-logs (for example as compared to no treatment or treatment with a plant extract alone without silver ions).

Immobilized: Bound to a surface, such as a solid support. In one embodiment, the solid surface is in the form of a towel or wipe. In some examples, the disclosed antimicrobial compositions are immobilized to a support by simply applying the composition in solution to the support, thereby immobilizing the composition to the support.

Microorganism: Any of various bacteria, viruses, fungi, and protozoa that can cause disease or death to humans, animals, or plants, or other biological organisms. Pathogenic spores are spores that are produced from a pathogen. Particular examples of pathogens that can produce spores include, but are not limited to, members of the genera *Bacillus, Clostridium, Desulfotomaculans, Sporolactobacillus, Sporpsarcina* and pathogenic fungi. In some examples the spore is referred to as an oocyst, such as those produced by members of the Phylum Apicomplexa (such as *Plasmodium falciparum* and *Cryptosporidium parvum*).

Viable: Capable of living, developing, or germinating under favorable conditions. For example, a viable pathogen is capable of developing under favorable conditions.

Overview

Antimicrobials from plants are a possible alternative to current sanitizers and disinfectants. Plant essential oils may be used in situations in which the use of other antimicrobials is not advantageous; for instance, in applications in which chemical antimicrobials have limited efficacy or because of concerns over the production of harmful disinfectant by-products.

Many plant antimicrobials are membrane active. For instance, carvacrol, found in oregano, partitions the fatty acid chains of cell membrane phospholipids, thus forming ion channels which permit ions to escape the cytoplasm (Cox and Markham 2007).

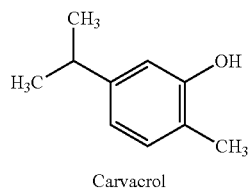

Carvacrol

Citral, the active component of lemongrass, is a type of terpenoid that causes the leakage of specific ions because its action on the cell membrane has dramatic effects on proton motive forces, the intracellular ATP content, and the overall cell activity (Somolinos et al., 2010).

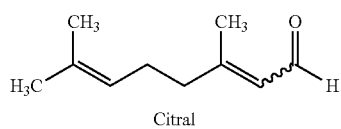

Citral

Allspice attributes its antimicrobial capabilities to its primary active component eugenol that has a variety of antioxidant properties (Masahiro et al. 2000) such as the scavenging of radicals and the chelating of metal ions. Eugenol also reportedly participates in photochemical reactions (Mihara and Shibamoto 1982). Thus, in some examples the disclosed antimicrobial compositions include eugenol.

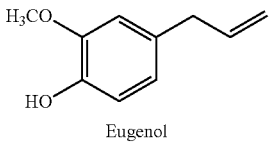

Eugenol

Cinnamaldehyde, the major active component in cinnamon oil, disrupts enzyme activity (Ravishankar et al., 2010).

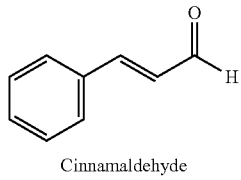

Cinnamaldehyde

Silver (Ag) ion has been used as a disinfectant since antiquity. It is known to bind to disulfide (S—S) and sulfhydryl (—SH) groups on proteins in microbial cell walls, interfering in critical membrane transport and biochemical pathways (Silvestry-Rodriguez et al., 2007b). Silver has demonstrated efficacy against yeasts, viruses, and a wide variety of bacteria (Silvestry-Rodriguez et al. 2007b).

Unlike numerous other antimicrobials, silver is not considered a hazardous substance (Ibarluzea et al., 1998; Kim et al., 2002; who.int/water_sanitation_health/dwq/chemicals/silver.pdf). Both the U.S. Environmental Protection Agency (EPA) and the World Health Organization (WHO) regard silver as safe for human consumption (Silvestry-Rodriguez et al., 2007b; epa.gov/safewater/mcl.html; who.int/water_sanitation_health/dwq/chemicals/silver.pdf). The only known side effect of silver consumption in humans is argyria (irreversible skin discoloration) and argyrosis (discoloration of the eye), which only occur with the ingestion of regular gram quantities of silver over several years or by the administration of high concentrations to ill individuals. These conditions are not dangerous, but are cosmetically undesirable (Lansdown 2006). The amount of silver needed to achieve the desired antimicrobial effect is usually on the order of 10 to 100 parts per billion (µg/l or ppb). Based on our previous work, for a 1000 ppb silver treatment on 10 grams of lettuce, the amount remaining on the lettuce after treatment was approximately 0.06 µg/g. Assuming that a person consumes 200 g of lettuce 365 d per year, after 76 years they will have consumed 0.333 g of silver. Based on epidemiological and pharmacokinetic data, a lifetime limit of 10 g of silver is considered a No Observable Adverse Effect Level (NOAEL) for humans (who.int/water_sanitation_health/dwq/chemicals/silver.pdf). Thus, it would therefore require more than 2,280 years before enough silver would be consumed to cause any adverse effects.

As such, silver has been used in numerous applications in which it is either ingested or comes into contact with exposed tissues. For instance, silver has been used in Mexico for more than 50 years in commercially available consumer fruit and vegetable washes such as Microdyn®, BacDyn® plus, Biopur®, Bacterin®, and Gadicin® Argentum, among others. In the U.S., silver has also been used to coat medical devices such as catheters (Gentry and Cope 2005) and bandages for large open wounds or burns (Silver 2003). Silver is also commonly used to prevent biofilm formation in commercial household water purification units. These are known to leach silver into the filtered water at levels up to 50 ppb (Silvestry-Rodriguez et al., 2007b).

Silver has been used in combination with a variety of membrane active antimicrobials such as oxidizers (e.g., chlorine), producing additive and sometimes synergistic antimicrobial effects (Yahya et al., 1992; Armon et al., 2000; Butkus et al., 2004, Silvestry-Rodriguez et al., 2007b). Synergy occurs when two agents working in concert exert a greater antimicrobial effect than merely the sum of their individual effects. Such synergy can result in the use of lower concentrations of each antimicrobial, potentially lowering the costs and reducing the risks of toxicity (Privett et al., 2010). It has been postulated that the oxidizer disrupts the cell wall and effects the rapid penetration of silver into the cell, where irreversible precipitation of the DNA occurs (Yahya et al., 1992; Armon et al., 2000).

Unlike other sanitizers/disinfectants such as ozone, chlorine, and hydrogen peroxide, plant antimicrobials and silver are not as sensitive to the presence of organic matter (Silvestry-Rodriguez et al., 2007a; Matthews 2009). As a result, they should retain their antimicrobial efficacy for longer periods and should not require the frequency of application or monitoring of antimicrobial solutions as many traditionally used antimicrobials. In addition, since both the plant antimicrobials and silver are considered safe for human consumption at these levels, these antimicrobials may be used in applications in which other antimicrobials are considered unsafe. Finally, some plant antimicrobials can be fairly expensive to produce due to the costs associated with their extraction and purification. Although silver is considered a precious metal, it is quite inexpensive (costing a small fraction of a U.S. cent) at the concentrations (e.g., 100 ppb) required to produce such a synergistic effect. Therefore, combining these highly effective plant antimicrobials with silver provides a more cost-effective and non-toxic product that is a feasible option for a variety of sensitive applications.

Although silver is an effective antimicrobial, it requires hours to produce a significant reduction in bacterial populations. Therefore, not surprisingly, no reductions were observed within the 30-min time scale of the experiments included herein for the silver alone treatments. Thus, any enhanced reduction when combined with a plant antimicrobial may be attributed to antimicrobial synergy.

Several plant antimicrobials were found to be synergistic with silver ions when combined in solution, producing more rapid and significant reductions in *E. coli* populations than the individual antimicrobials alone. These plant antimicrobials were highly effective at concentrations of 0.04% carvacrol, 0.1% citral, 0.2% cinnamaldehyde, and 1.0% allspice, eliciting >5.0-$\log_{10}$ reductions within 1 to 10 min of exposure; however, in the current study with the focus of determining the amount of synergy between these compounds and silver, the concentrations were halved (0.02% carvacrol, 0.05% citral, 0.1% cinnamaldehyde, and 0.5% allspice) so that they would only yield partial reductions of the bacterial population. Thus, any enhanced antimicrobial effect due to the addition of silver could then be observed and quantified. However, not all plant extracts were effective in combination with silver. For example, it is shown herein that olive extract alone are effective antimicrobials, but combination with silver ions had an antagonistic effect rather than a synergistic effect on antimicrobial activity.

The results for each of the plant antimicrobials alone or in combination with silver are shown in Tables 1 through 4. No significant reductions were observed with the Ag treatment within 30 min of exposure for any of the experiments.

The effectiveness of citral, cinnamaldehyde, carvacrol, and allspice oils were determined against *Escherichia coli* in vitro. In addition, since many plant compounds are believed to be membrane-active, silver ions were included to assess the potential for synergy. Silver ions, although slow-acting, often (but not always) exhibit synergistic antimicrobial efficacy when combined with membrane-active agents such as oxidizers. All four essential oils produced significant reductions (P≤0.05) of >5.0-$\log_{10}$ in bacterial populations within one to 10 minutes of exposure. In combination with silver, these treatments produced more rapid and statistically significant reductions in *E. coli* than either the silver or plant antimicrobials individually. Thus, synergy was observed in which smaller amounts of the plant compounds were needed when combined with silver ions to produce similar effects. The use of such combinations can therefore result in highly effective and inexpensive antimicrobial treatments that can be used in a wide variety of applications.

Antimicrobial Compositions

Provided herein are antimicrobial compositions. The disclosed compositions include one of more of citral, cinnamaldehyde, carvacrol, and allspice (such as citral oil, cinnamaldehyde oil, carvacrol oil, and/or allspice oil), in combination with silver ions. In some examples, one or more of the citral, cinnamaldehyde, carvacrol, and/or allspice are provided in the form of an oil, however, in some examples one or more are provided as a solid. In some examples, the remainder of the composition is water, phosphate buffered saline (PBS), or a mixture of PBS and ethanol (such as no more than 5% ethanol).

In one example, the antimicrobial composition includes citral and silver ions. For example, the citral can be present in the composition at a concentration of at least about 0.01% vol/vol, such as at least about 0.025% vol/vol, at least about 0.05% vol/vol, at least about 0.06% vol/vol, at least about 0.07% vol/vol, at least about 0.08% vol/vol, at least about 0.09% vol/vol, at least about 0.1% vol/vol, for example 0.01% vol/vol, 0.025% vol/vol, 0.05% vol/vol, 0.06% vol/vol, 0.07% vol/vol, 0.08% vol/vol, 0.09% vol/vol, or 0.1% vol/vol. In some examples, the citral is present in the composition at a concentration of 0.01% to 0.5% vol/vol, 0.025% to 0.25% vol/vol, 0.04% to 0.2% vol/vol, or 0.05% to 0.1% vol/vol.

In one example, the antimicrobial composition includes cinnamaldehyde and silver ions. For example, the cinnamaldehyde can be present in the composition at a concentration of at least about 0.01% vol/vol, such as at least about 0.025% vol/vol, at least about 0.05% vol/vol, at least about 0.06% vol/vol, at least about 0.075% vol/vol, at least about 0.1% vol/vol, at least about 0.15% vol/vol, at least about 0.2% vol/vol, for example 0.01% vol/vol, 0.025% vol/vol, 0.05% vol/vol, 0.075% vol/vol, 0.1% vol/vol, 0.2% vol/vol, 0.3% vol/vol, or 0.5% vol/vol. In some examples, the cinnamaldehyde is present in the composition at a concentration of 0.01% to 0.5% vol/vol, 0.05% to 0.5% vol/vol, 0.05% to 0.3% vol/vol, or 0.1% to 0.2% vol/vol.

In one example, the antimicrobial composition includes carvacrol and silver ions. For example, the carvacrol can be present in the composition at a concentration of at least about 0.005% vol/vol, such as at least about 0.001% vol/vol, at least about 0.01% vol/vol, at least about 0.02% vol/vol, at least about 0.03% vol/vol, at least about 0.04% vol vol$^{-1}$, at least about 0.05% vol/vol, at least about 0.06% vol/vol, at least about 0.07% vol vol$^{-1}$, at least about 0.08% vol/vol, at least about 0.09% vol/vol, at least about 0.1% vol vol$^{-1}$, for example 0.01% vol/vol, 0.02% vol/vol, 0.03% vol/vol, 0.04% vol vol$^{-1}$, 0.05% vol/vol, 0.08% vol/vol, or 0.1% vol/vol. In some examples, the carvacrol is present in the composition at a concentration of 0.005% to 0.1% vol/vol, 0.01% to 0.1% vol/vol, 0.01% to 0.05% vol/vol, or 0.02% to 0.04% vol/vol.

In one example, the antimicrobial composition includes allspice oil and silver ions. For example, the allspice oil (or eugenol) can be present in the composition at a concentration of at least about 0.05% vol/vol, such as at least about 0.1% vol/vol, at least about 0.2% vol/vol, at least about 0.3% vol/vol, at least about 0.4% v vol/vol, at least about 0.5% vol/vol, at least about 0.6% vol/vol, at least about 0.7% vol/vol, at least about 0.8% vol/vol, at least about 0.9% vol/vol, at least about 1% vol/vol, for example 0.1% vol/vol, 0.2% vol/vol, 0.3% vol/vol, 0.4% vol/vol, 0.5% vol/vol, 0.6% vol/vol, 0.7% vol/vol, 0.8% vol/vol, 0.9% vol/vol, 1% vol/vol, 1.25% vol/vol, or 1.5% vol/vol. In some examples, the allspice oil (e.g., eugenol) is present in the composition at a concentration of 0.05% to 5% vol/vol, 0.05% to 2.5% vol/vol, 0.5% to 2.5% vol/vol, or 0.5% to 1% vol/vol.

In one example, the silver ions are present in the composition at a concentration of at least about 1 part per billion (ppb), such as at least about 2 ppb, such as at least about 3 ppb, such as at least about 4 ppb, such as at least about 5 ppb, such as at least about 10 ppb, such as at least about 20 ppb, such as at least about 30 ppb, such as at least about 40 ppb, such as at least about 50 ppb, such as at least about 60 ppb, such as at least about 70 ppb, such as at least about 80 ppb, such as at least about 90 ppb, such as at least about 100 ppb, or such as at least about 200 ppb, for example 1 ppb, 5 ppb, 10 ppb, 20 ppb, 30 ppb, 40 ppb, 50 ppb, 60, ppb, 70 ppb, 80 ppb, 90 ppb, 100 ppb, 150 ppb, 200 ppb, or 250 ppb. In some examples, the silver ions are present in the composition at a concentration of 1 to 500 ppb, 1 to 250 ppb, 1 to 100 ppb, 5 to 100 ppb, or 10 to 100 ppb.

In some examples, the disclosed antimicrobial compositions include a combination of plant oils in combination with silver ions, such as two, three, or all four of citral, cinnamaldehyde, carvacrol, and allspice in combination with silver ions.

The disclosed antimicrobial compositions can include other agents, such as water and/or ethanol. In some examples, since the composition can be an aqueous cleaner, the principal ingredient can be water, such as at a level of at least about 70%, at least about 80%, at least about 90%, at least about 95%, at least 98%, or at least 99%, such as 70-99%, 70-95%, or 80-98% vol/vol. Distilled, deionized, or industrial soft water can be used.

In some examples, the disclosed antimicrobial compositions include an acid, such as nitric acid, acetic acid, glycolic acid, lactic acid or propionic acid, to stabilize the silver in the composition. In some examples, the disclosed antimicrobial compositions further include one or more solvents, surfactants, cosurfactants, chelating agents, buffers, thickeners, dyes, colorants, fragrances, defoamers, and combinations thereof.

In some examples, the disclosed antimicrobial compositions are liquids. Thus, such compositions can be formulated in a spray, for example provided in a container that permits dispensing of the antimicrobial composition. Such a container can be made of plastic, glass, or the like.

In some examples, the disclosed antimicrobial composition is liquid, but is provided on a solid support, such as a layer of absorbent/adsorbent material (such as a wipe). Such wipes can be provided in a container that permits the wipes to be dispensed, such as one at a time. Such a wipe can be impregnated with a liquid antimicrobial composition provided herein.

Exemplary Substrates

The substrate for the wipe containing the disclosed antimicrobial compositions is generally an absorbent or adsorbent material. In some examples, it is a nonwoven sheet, which is at least one layer, made of wood pulp; or a blend of wood pulp and a synthetic fiber, such as polyester, rayon, nylon, polypropylene, polyethylene, other cellulose polymers; or a synthetic fiber or mixture of such fibers. The nonwovens can include nonwoven fibrous sheet materials such as meltblown, coform, air-laid, spun bond, wet laid, bonded-carded web materials, hydroentangled materials, and combinations thereof. These materials can include synthetic or natural fibers or combinations thereof. A binder may or may not be present. Such supports are commercially available, for example from Kimberly-Clark, E.I. du Pont de Nemours and Company, Dexter, American Nonwovens, James River, BBA Nonwovens and PGI. Examples of such substrates are depicted or described in: U.S. Pat. Nos. 4,781,974, 4,615,937, U.S. Pat. No. 4,666,621, U.S. Pat. No. 6,340,663, WO 98/03713, U.S. Pat. No. 5,908,707, WO 97/40814, WO 96/14835 and EP 750063.

Woven materials, such as cotton fibers, cotton/nylon blends, or other textiles may also be used. Regenerated cellulose, polyurethane foams, and the like, which are used in making sponges, can also be suitable.

The substrate's liquid loading capacity in some examples is at least about 50%-1000% of the dry weight thereof, such as at least about 200%-800%. This is expressed as loading ½ to 10 times the weight (or, more accurately, the mass) of the substrate.

The substrate can in particular examples be about 0.01 to about 1,000 grams/m$^2$, such 25 to 120 grams/m$^2$ (referred to as "basis weight") and typically is produced as a sheet or web which is cut, die-cut, or otherwise sized into the appropriate shape and size.

The substrates, which can be referred to simply as a wipe, can be individually sealed with a heat-sealable or glueable thermoplastic overwrap (such as polyethylene, Mylar, and the like). The wipes can be packaged as numerous, individual sheets which are then impregnated or contacted with the liquid antimicrobial compositions provided herein for more economical dispensing. The wipes can be formed as a continuous web during the manufacturing process and loaded into a dispenser, such as a canister with a closure, or a tub with closure. The closure is to seal the moist wipes from the external environment and to prevent premature volatilization of the liquid ingredients. In some examples, the dispenser is formed of plastic, such as high density polyethylene, polypropylene, polycarbonate, polyethylene pterethalate (PET), polyvinyl chloride (PVC), or other rigid plastics. However, other materials are possible, such as glass or ceramic dispensers. The continuous web of wipes can be threaded through a thin opening in the top of the dispenser, such as through the closure. A means of sizing the desired length or size of the wipe from the web can be provide. A knife blade, serrated edge, or other means of cutting the web to desired size can be provided on the top of the dispenser, for non-limiting example, with the thin opening actually doubling in duty as a cutting edge. Alternatively, the continuous web of wipes could be scored, folded, segmented, or partially cut into uniform or non-uniform sizes or lengths, which would then obviate the need for a sharp cutting edge. Further, as in hand tissues, the wipes could be interleaved, so that the removal of one wipe advances the next, and so forth.

The wipes can have a certain wet tensile strength of about 25 to about 250 Newtons/m, such as about 75-170 Newtons/m.

Applying the Liquid Antimicrobial Solution to the Solid Substrate

The disclosed liquid antimicrobial compositions can be impregnated, dosed, loaded, metered, or otherwise dispensed onto the solid substrate/wipe. Such methods are known in the art. For example, each individual wipe can be treated with a discrete amount of liquid. In another example, a continuous web of wipes is treated in mass with the liquid. In some cases, an entire web of wipes is soaked in the liquid. In other cases, while the web is being spooled, or even during the creation of the nonwoven material, the liquid cleaner is sprayed or otherwise metered onto the web. A mass, such as a stack of individually cut and sized wipes can also be impregnated in its container.

Exemplary Surfactants

In some examples, the disclosed antimicrobial compositions include a surfactant, such as a low residue surfactant, for example a glycoside such as an alkyl polyglycosides. Exemplary glycoside surfactants that can be used include but are not limited to Glucopon 225, Glucopon 220, Glucopon 325, Glucopon 625, Glucopon 600 (the Henkel Corporation) and Triton CG-110 (Union Carbide).

Glucoside surfactants are frequently supplied as mixtures with other surfactants. For example, mixtures with the anionic surfactants, lauryl sulfate or laurylether sulfate, or the amphoteric surfactants, cocamidopropylbetaine or cocamidopropyl aminoxide, are available from the Henkel Corporation.

The amounts of surfactants present are generally about 0.001-6% (wt/vol), more preferably 0.002-4.00% surfactant (wherein the % is the weight percent (based on 100% active) of the composition).

Exemplary Cosurfactants

In some examples, the disclosed antimicrobial compositions include one or more cosurfactants, for example to obtain additional cleaning benefits. A glycoside surfactant may be used in conjunction with any of the other nonionic, anionic, cationic or amphoteric surfactants, or mixtures thereof, such as are known in the art. Such surfactants are described, for example, in McCutcheon's Emulsifiers and Detergents (1997).

Exemplary nonionic surfactants include the ethylene oxide and mixed ethylene oxide/propylene oxide adducts of alkylphenols, the ethylene oxide and mixed ethylene oxide/propylene oxide adducts of long chain alcohols or of fatty acids, mixed ethylene oxide/propylene oxide block copolymers, esters of fatty acids and hydrophilic alcohols, such as sorbitan monooleate, alkanolamides, and the like.

Exemplary anionic surfactants include soaps, alkylbenzene sulfonates, olefin sulfonates, paraffin sulfonates, alcohol and alcohol ether sulfates, phosphate esters, and the like.

Exemplary cationic surfactants include amines, amine oxides, alkylamine ethoxylates, ethylenediamine alkoxylates such as the Tetronic® series from BASF, quaternary ammonium salts, and the like.

Exemplary amphoteric surfactants are those which have both acidic and basic groups in their structure, such as amino and carboxyl radicals or amino and sulfonic radicals, or amine oxides and the like. Suitable amphoteric surfactants include betaines, sulfobetaines, imidazolines, and the like.

The amounts of cosurfactants will generally be about less than the level of the primary low residue surfactant, such as glycoside.

Exemplary Chelating Agents

In some examples, the disclosed antimicrobial compositions include one or more chelating agents. Exemplary chelants that can be used include the various alkali metal, ammonium and substituted ammonium polyacetates, carboxylates, polycarboxylates and polyhydroxysulfonates. Non-limiting examples of polyacetate and polycarboxylate builders include the sodium, potassium, lithium, ammonium and substituted ammonium salts of ethylenediamine tetraacetic acid, ethylenediamine triacetic acid, ethylenediamine tetrapropionic acid, diethylenetriamine pentaacetic acid, nitrilotriacetic acid, oxydisuccinic acid, iminodisuccinic acid, mellitic acid, polyacrylic acid or polymethacrylic acid and copolymers, benzene polycarboxylic acids, gluconic acid, sulfamic acid, oxalic acid, phosphoric acid, phosphonic acid, organic phosphonic acids, acetic acid, and citric acid. These chelating agents may also exist either partially or totally in the hydrogen ion form, for example, citric acid or disodium dihydrogen ethylenediamine tetraacetate. The substituted ammonium salts include those from methylamine, dimethylamine, butylamine, butylenediamine, propylamine, triethylamine, trimethylamine, monoethanolamine, diethanolamine, triethanolamine, isopropanolamine, and propanolamine.

Other chelating agents, and dependent on the desired pH of the formulation, are the mono-, di-, tri-, and tetrapotassium and ammonium salts of ethylenediamine tetraacetic acid.

The amount of chelant in the composition can in the range of 0.001-2%, such as 0.001-2%, by weight of the liquid composition.

Exemplary Solvents

A solvent may optionally be included in the composition. The solvent is generally a water soluble or dispersible organic solvent having a vapor pressure of at least 0.001 mm Hg at 25° C. In some examples, the solvent volatilizes rapidly, such that it volatilizes no more than 5 minutes after contact with a surface. In some examples the solvent is a $C_{1-6}$ alkanols, $C_{1-6}$ diols, $C_{1-6}$ alkyl ethers of alkylene glycols and polyalkylene glycols, and mixtures thereof. The alkanol can be methanol, ethanol, n-propanol, isopropanol, the various positional isomers of butanol, pentanol, and hexanol, and mixtures thereof. It may also be possible to utilize in addition to, or in place of, said alkanols, the diols such as methylene, ethylene, propylene and butylene glycols, and mixtures thereof, and including polyalkylene glycols.

In one example the solvent is a straight or branched chain alkanol, such as methanol, ethanol, n-propanol, isopropanol, and the various positional isomers of butanol, pentanol, and hexanol. A mixture of an alkanol with a glycol ether can be used, in which the ratio of the two components is about 100:1 to 1:10.

In one example the solvent is an alkylene glycol ether solvent. These can include, for example, monoalkylene glycol ethers such as ethylene glycol monopropyl ether, ethylene glycol mono-n-butyl ether, propylene glycol monopropyl ether, and propylene glycol mono-n-butyl ether, and polyalkylene glycol ethers such as diethylene glycol monoethyl or monopropyl or monobutyl ether, di- or tri-polypropylene glycol monomethyl or monoethyl or monopropyl or monobutyl ether, etc., and mixtures thereof. Additionally, acetate and propionate esters of glycol ethers can be used.

Short chain carboxylic acids, such as acetic acid, glycolic acid, lactic acid and propionic acid can also be used. Short chain esters, such as glycol acetate, or cyclic or linear volatile methylsiloxanes (such as from Dow Corning), can also be used.

Additional water insoluble solvents can be included in minor amounts (0-1%). These include isoparafinic hydrocarbons, mineral spirits, alkylaromatics, and terpenes such as d-limonene. Additional water soluble solvents may be included in minor amounts (0-2%). These include pyrrolidones, such as N-methyl-2-pyrrolidone, N-octyl-2-pyrrolidone and N-dodecyl-2-pyrrolidone.

The total amount of solvents is usually no more than about 20%, such as no more than about 10%, such as 1-5% (wt/vol or vol/vol), of the liquid composition. These amounts of solvents are generally referred to as dispersion-effective or solubilizing-effective amounts.

Exemplary Miscellaneous Adjuncts

Buffering and pH adjusting agents can be included in the antimicrobial composition. Examples include minute amounts of inorganic agents such as alkali metal and alkaline earth salts of silicate, metasilicate, borate, carbonate, carbamate, phosphate, ammonia, and hydroxide. Organic buffering agents such as monoethanolamine, monopropanolamine, diethanolamine, dipropanolamine, triethanolamine, and 2-amino-2-methylpropanol can be included.

Small amounts of adjuncts can be added for improving aesthetic qualities of the disclosed compositions. Aesthetic adjuncts include fragrances or perfumes, such as those available from Givaudan-Rohre, International Flavors and Fragrances, Quest, Sozio, Firmenich, Dragoco, Norda, Bush Boake and Allen and others, and dyes or colorants which can be solubilized or suspended in the formulation. Further solubilizing materials, such as hydrotropes (e.g., water soluble salts of low molecular weight organic acids such as the sodium or potassium salts of xylene sulfonic acid), may also be desirable. Adjuncts for cleaning include additional surfactants, such as those described in Kirk-Othmer, Encyclopedia of Chemical Technology, 3rd Ed., Volume 22, pp. 332-432 (Marcel-Dekker, 1983), and McCutcheon's Soaps and Detergents (N. Amer. 1984). Dyes or colorants which can be solubilized or suspended in the formulation, such as diaminoanthraquinones, may be added. Thickeners, such as polyacrylic acid, xanthan gum, alginates, guar gum, methyl, ethyl and propylhydroxycelluloses, and the like can be included. Defoamers, such as, without limitation, silicones, aminosilicones, silicone blends, silicone/hydrocarbon blends, and the like, available from Dow Corning, Wacker, Witco, Ross and Hercules, can be included.

The amounts of these aesthetic adjuncts can in some examples be in the range of 0-2%, such as 0-1% wt/vol or vol/vol.

Antimicrobial Methods

Methods of using the disclosed compositions as a decontaminant, for example to kill undesired microorganisms or pathogens, are provided herein. The methods can be used to decontaminate an article (such as laboratory equipment, a produce item, or raw meat) or a surface (such as those in a building, house, office, food processing plant, cargo holds on transportation vessels such as airplanes, trucks, trains and ships) that is actually or potentially contaminated with one or more undesired microorganisms. Thus, the disclosed methods can be used to decontaminate a surface (such as a hard surface), for example by killing microorganisms on the surface. For example, the surface to be decontaminated, for example by killing microorganisms present on the surface, can be contacted with the composition, for example by applying the composition to the surface (e.g., by pouring or spraying the composition onto the surface, or by wiping the surface with a solid substrate containing the composition, such as a towel or wipe). In some examples, the surface to be decontaminated is an article, such as a produce or meat or fish item. In such examples, to decontaminate the article, for example by killing microorganisms present on the surface of the article, the article can be contacted with the composition, for example by applying the composition to the surface (e.g., by pouring or spraying the composition onto the surface, by wiping the surface with a solid substrate containing the composition, such as a towel or wipe), or by immersing the article in a container containing the composition.

Thus, the disclosed methods can be used to kill microorganisms present on a surface, such as surfaces found in a home, business, or industry (such as a business that processes food). The surface may contain undesired microorganisms. Exemplary surfaces include those found in a home (e.g., counter tops, floors, cutting boards, toilets, sinks, showers, tubs, and the like), in an office building (e.g., desk tops, tables, computer mouse, computer keyboard, door knobs, copy machines, and the like), in a food processing building (such as surfaces that commonly come in contact with food, such as storage containers, processing surfaces, washing areas, and the like) as well as vessels used to transport food, such as surfaces (such as storage areas in an airplane, truck, train or ship). Thus, hard surfaces can be decontaminated with the disclosed compositions.

Examples of articles that can be decontaminated with the disclosed compositions include, but are not limited to, laboratory equipment, such as refrigerators, centrifuges, incubators, water baths, and so on. In one example, the item to be decontaminated is a produce item, such as the surface of a fruit or vegetable, such as tomatoes, lettuce, spinach, herbs, radishes, onions, scallions, alfalfa sprouts, cucumbers, apples, grapes, peaches, nectarines, plums, berries, cantaloupes, and the like. In some examples, the item to be decontaminated is a meat item, such as a piece of raw meat from a cow, pig, or chicken, such as chicken breasts, thighs, wings, or legs, steaks, ground beef, ribs, roasts, and the like. In some examples, the item to be decontaminated is a seafood item, such as a fish or shellfish. Thus, the disclosed compositions can be used to kill adulterants in food products, such as a pathogen.

Thus, provided herein are methods of killing a microorganism (e.g., bacterium, bacterial spore, fungal spore, protozoan, or virus), by contacting the microorganism with the antimicrobial composition provided herein. In one example, the bacterium killed is *Escherichia coli*. In some examples, the microorganism is killed within 10 minutes, within 15 minutes, within 20 minutes, or within 30 minutes (such as within 10-30 minutes, 10-20 minutes or 10-15 minutes) of contacting it with the antimicrobial composition. In some examples, not all of the microorganisms contacted with the composition are killed, but the composition is still an antimicrobial composition. For example, in some examples at least 90%, at least 95%, at least 99%, at least 99.9%, at least 99.99%, or at least 99.999% of the microorganisms (such as an at least 10-fold, at least 20-fold, at least 30-fold, at least 40-fold, at least 50-fold, or at least 100-fold reduction) are killed within 10 minutes, within 20 minutes, or within 30 minutes (such as within 10-30 minutes, 10-20 minutes or 10-15 minutes) of contacting it with the antimicrobial composition.

In some examples, the method reduces a number of viable microorganisms by at least 4-$\log_{10}$ within at least 1 minute of exposure to the antimicrobial composition, such as within 2 minutes, within 3 minutes, within 4 minutes, within 5 minutes, within 6 minutes, within 7 minutes, within 8 minutes, within 9 minutes, within 10 minutes, within 11 minutes, within 12 minutes, within 13 minutes, within 14 minutes, within 15 minutes, within 16 minutes, within 17 minutes, within 18 minutes, within 19 minutes, within 20 minutes, within 12 minutes, within 22 minutes, within 23 minutes, within 24 minutes, within 25 minutes, within 26 minutes, within 27 minutes, within 28 minutes, within 29 minutes, or within 30 minutes of exposure to the antimicrobial composition. Thus, in some examples, the method reduces a number of viable microorganisms by at least 4-$\log_{10}$ (such as at least 5-$\log_{10}$, at least 6-$\log_{10}$, at least 7-$\log_{10}$, or at least 8-$\log_{10}$) within 1-10 minutes, 1-5 minutes, or 1-15 minutes of exposure to the antimicrobial composition.

In some examples, the method reduces a number of viable microorganisms by at least 5-fold more within at least 1 minute of exposure as compared to contacting the microorganisms with citral, cinnamaldehyde, carvacrol, or allspice without silver, such as within 2 minutes, within 3 minutes, within 4 minutes, within 5 minutes, within 6 minutes, within 7 minutes, within 8 minutes, within 9 minutes, within 10 minutes, within 15 minutes, or within 30 minutes of exposure. Thus, in some examples, the method reduces a number of viable microorganisms by at least 5-fold (such as at least 10-fold, at least 20-fold, at least 25-fold, at least 30-fold, at least 40-fold, at least 50-fold, at least 100-fold or at least 1000-fold) within 1-10 minutes, 1-5 minutes, or 1-15 minutes of exposure to the antimicrobial composition as compared to contacting the microorganisms with citral, cinnamaldehyde, carvacrol, or allspice without silver.

Methods for assaying for pathogen growth or viability are known in the art. Although particular examples are provided herein, the disclosure is not limited to such methods.

In some examples, the method can include rinsing the surface after it has been contacted with the antimicrobial composition, for example the surface can be rinsed with water. In a specific example, the surface is a meat or fish product that is rinsed with water after it has been contacted with the antimicrobial composition.

Pathogens/Microorganisms

In some examples, the disclosed compositions can be used to reduce the number of, for example kill, a pathogen or microorganism. For example, particular microorganism or even undesired spores can be disinfected with the disclosed antimicrobial compositions. Exemplary pathogens that can be killed with the disclosed antimicrobial compositions include, but are not limited to, viruses, bacteria, fungi, nematodes, and protozoa, as well as spores (e.g., bacterial and fungal spores). In some examples, the microorganism killed is a food spoilage microorganism. A non-limiting list of pathogens that can be killed using the antimicrobial compositions provided herein are provided below.

For example, viruses that can be killed using the antimicrobial compositions provided herein include both enveloped and non-enveloped positive-strand RNA viruses and negative-strand RNA viruses. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepataviridae (e.g., Hepatitis A viruses); Hepeviridae (such as Hepatitis E virus); Togaviruses (examples of which include rubella; alphaviruses (such as Western equine encephalitis virus, Eastern equine encephalitis virus, and Venezuelan equine encephalitis virus)); Astroviridae (such as Astroviruses), Flaviviruses (examples of which include Dengue virus, West Nile virus, and Japanese encephalitis virus); Calciviridae (which includes Norovirus and Sapovirus); and Coronaviruses (examples of which include the MERS coronavirus and the SARS coronaviruses, such as the Urbani strain). Exemplary negative-strand RNA viruses include, but are not limited to: Orthomyxyoviruses (such as the influenza virus), Rhabdoviruses (such as Rabies virus), and Paramyxoviruses (examples of which include measles virus, respiratory syncytial virus, and parainfluenza viruses).

Viruses also include double-stranded RNA viruses. Double stranded RNA viruses that can be killed using the antimicrobial compositions provided herein include, but are not limited to Reoviridae (such as the Rotaviruses).

Viruses also include DNA viruses. DNA viruses that can be killed using the antimicrobial compositions provided herein include, but are not limited to: Herpesviruses (such as Varicella-zoster virus, for example the Oka strain; cytomegalovirus; and Herpes simplex virus (HSV) types 1 and 2); Hepadnaviridae (such as Hepatitis B virus); Adenoviruses (such as Adenovirus type 1, Adenovirus type 40, and Adenovirus type 41); Poxviruses (such as Vaccinia virus); and Parvoviruses (such as Parvovirus B19).

Another group of viruses includes Retroviruses. Examples of retroviruses that can be killed using the antimicrobial compositions provided herein include, but are not limited to: human immunodeficiency virus type 1 (HIV-1), such as subtype C; HIV-2; equine infectious anemia virus; feline immunodeficiency virus (FIV); feline leukemia viruses (FeLV); simian immunodeficiency virus (SIV); and avian sarcoma virus.

In one example, the virus killed with the disclosed antimicrobial compositions is one or more of the following: HIV (for example an HIV antibody, p24 antigen, or HIV genome); Hepatitis A virus (for example an Hepatitis A antibody, or Hepatitis A viral genome); Hepatitis B (HB) virus (for example an HB core antibody, HB surface antibody, HB surface antigen, or HB viral genome); Hepatitis C (HC) virus (for example an HC antibody, or HC viral genome); Hepatitis D (HD) virus (for example an HD antibody, or HD viral genome); Hepatitis E virus (for example a Hepatitis E antibody, or HE viral genome); a respiratory virus (such as influenza A & B, respiratory syncytial virus, human parainfluenza virus, or human metapneumovirus), or West Nile Virus.

Pathogens also include bacteria. Bacteria can be classified as Gram-negative, Gram-positive, or Acid Fast. Exemplary Gram-negative bacteria that can be killed using the antimicrobial compositions provided herein include, but are not limited to: *Escherichia coli* (e.g., K-12, O157:H7, other shiga-toxin producing strains [STEC]), *Salmonella enterica, Campylobacter jejuni, Shigella dysenteriae, Legionella pneumophila, Neisseria gonorrhoeae*, and *Vibrio* species (such as *V. cholerae, V. vulnificus, V. parahaemolyticus*). Exemplary Gram-positive bacteria that can be killed using the antimicrobial compositions provided herein include, but are not limited to: *Bacillus anthracis, Staphylococcus aureus* (e.g., methicillin resistant *S. aureus*), *Enterococcus* species (such as vancomycyin resistant Enterococci), *Listeria mono-* cytogenes, Clostridium species (e.g., Clostridium difficile, Clostridium perfringens), pneumococcus, gonococcus, and streptococcal meningitis. Exemplary Acid fast bacteria that can be killed using the antimicrobial compositions provided herein include, but are not limited to: Mycobacterium species (such as Mycobacterium tuberculosis, members of the Mycobacterium avium complex [MAC]) In one example, the bacteria killed with the disclosed methods is one or more of the following: Group A Streptococcus; Group B Streptococcus; Helicobacter pylori; Methicillin-resistant Staphylococcus aureus; Vancomycin-resistant enterococci; Clostridium difficile; E. coli (e.g., Shiga toxin producing strains); Listeria; Salmonella; Campylobacter; B. anthracis (such as spores); Chlamydia trachomatis; and Neisseria gonorrhoeae.

Protozoa, nemotodes, and fungi are also types of pathogens that can be killed using the antimicrobial compositions provided herein. Exemplary protozoa include, but are not limited to, Plasmodium (e.g., Plasmodium falciparum malaria), Leishmania, Acanthamoeba, Balmuthia mandrillaris, Giardia, Entamoeba, Cryptosporidium, Isospora, Balantidium, Trichomonas, Trypanosoma (e.g., Trypanosoma brucei, Trypanasoma cruzii), Naegleria fowleri, and Toxoplasma. Exemplary fungi include, but are not limited to: Saccharomyces, Candida albicans, Coccidiodes immitis, Stachybotrys chartarum, Blastomyces dermatitidis, and mildews.

In one example, bacterial spores are killed. For example, the genus of Bacillus and Clostridium bacteria produce spores that can be killed with the disclosed antimicrobial compositions. Thus, C. botulinum, C. difficile, C. perfringens, B. cereus, and B. anthracis spores can be killed (for example anthrax spores).

EXAMPLE 1

Materials and Methods

This example describes the materials and methods used in Examples 2-5 below.

Maintenance and Preparation of Bacterial Isolates

Escherichia coli strain 25922 was obtained from the American Type Culture Collection (ATCC; Manassas, Va., USA) and was maintained on Tryptic Soy Agar (TSA; Difco, Sparks, Md., USA) with incubation for 18 to 24 h at 37° C. Prior to the start of each experiment, an Erlenmeyer flask containing 100 ml of Tryptic Soy Broth (TSB; Difco, Sparks, Md., USA) was inoculated with the organism and incubated on an orbital shaker (Model G33; New Brunswick Scientific, Edison, N.J., USA) at 300 rpm at 37° C. overnight. After incubation, the E. coli were pelleted via centrifugation (9,820×g, 15 min, 20° C., JA-14 rotor, Beckman J2-21 centrifuge; Beckman Coulter, Inc., Fullerton, Calif., USA). The pelleted cells were washed by re-suspension in 100 ml of physiological saline (0.85% NaCl) followed by centrifugation as described previously. This step was repeated one additional time. The final pellet was resuspended in 10 ml of sterile phosphate buffered saline (PBS; pH 7.4; Sigma-Aldrich, St. Louis, Mo., USA). The test suspensions were then prepared by adding small volumes of the bacterial suspension to 10 ml of sterile PBS, resulting in an optical turbidity (measured using a BIOLOG turbidimeter, Hayward, Calif., USA) equivalent to a McFarland number 0.5 optical density standard [=$1.5\times10^8$ colony-forming units (CFU)/ml]. This solution was then diluted further in sterile PBS to achieve the desired final test concentration (approximately $1.0\times10^7$ CFU/ml).

Antimicrobials Preparation

A stock solution of silver (Ag) ions was prepared immediately prior to the start of each experiment by adding $AgNO_3$ (J.T. Baker, Phillipsburg, N.Y., USA) to distilled water to obtain an Ag ion concentration of 100 mg/l (100 ppm). The Ag concentration was measured at the beginning of each experiment by a colorimetric procedure using a Hach DR/2000 spectrophotometer (Anonymous 1989). A 10 µl volume of this stock was then added to test flasks containing 10 ml of PBS, resulting in a final silver concentration of 100 µg/l (100 ppb).

Allspice essential oil was obtained from Lhasa Karnak Herbal Co. (Berkley, Calif., USA). Citral (mixture of cis and trans, >96%), carvacrol (>98%), and cinnamaldehyde (93%) were purchased from Sigma-Aldrich (St. Louis, Mo., USA). The plant antimicrobials were dissolved and diluted (volume to volume) to specific test concentrations using PBS.

Experimental Protocol

The carvacrol, cinnamaldehyde, citral, and allspice were evaluated in separate experiments. The disinfection treatments for each experiment included the following: 1). 100 ppb silver, 2). The diluted plant antimicrobial, and 3). 100 ppb silver and the diluted plant antimicrobial. A control with E. coli in PBS but no added antimicrobials was also included. Purified stocks of the bacteria were added separately to the antimicrobial solutions (final concentration of ~$1.0\times10^7$ CFU/ml) and the flasks were placed on an orbital shaker (300 rpm) for the duration of the experiment. Experiments were performed in triplicate at room temperature (24° C.) in 50 ml polypropylene conical tubes (Becton, Dickinson and Company, Franklin Lakes, N.J., USA). At predetermined time intervals, 100 µl samples were collected and neutralized with Dey Engley (D/E) neutralizing broth (Difco, Sparks, Md., USA) at a ratio of 1:10. The D/E is neutralizes the antimicrobial effect of silver whereas the plant antimicrobials are neutralized via dilution. Samples were assayed for bacterial enumeration immediately.

Assay for Bacteria

Bacterial samples were ten-fold serially diluted in physiological saline as needed and the surviving bacteria were enumerated using the spread plate method on duplicate plates of Levine Eosin Methylene Blue Agar (EMB; Becton, Dickinson and Company, Franklin Lakes, N.J., USA). The plates were incubated at 37° C. for 24 hours and the surviving bacterial colonies were counted.

Statistical Analysis

Data were reported as logarithmic reduction using the formula $\log_{10}(N_0/N_t)$, where $N_0$ was the concentration of E. coli at time zero and $N_t$ was the surviving concentration at time t. A Student's t-test was used to determine if there were significant differences between the control and the antimicrobial treatments (the reductions were compared to the control after 30 min) or between the various treatments (for each exposure time). Differences were considered statistically significant if the resultant P value was ≤0.05.

EXAMPLE 2

Citral Alone or with Silver

Statistically significant (P≤0.05) reductions (compared to the control) were observed within 5 min of exposure (and each time interval thereafter) with both the citral alone and the citral combined with Ag treatments (Table 1). The reduction in E. coli observed for the combined citral/Ag treatment was greater than that observed with the individual citral treatment at each time interval. This difference between the two treatments was statistically significant (P≤0.05) after 10 and 20 min of exposure. There was no significant difference between the two treatments after 30 min of exposure; however, the reduction with the citral/Ag treatment had reached the limit of detection of the assay (50 CFU/m or >5.28 $\log_{10}$ reduction) and thus could potentially have been greater.

TABLE 1

Reduction ($\text{Log}_{10}$ ± standard deviation)* in the population of *Escherichia coli* after exposure to 0.05% citral (vol/vol) with and without silver (100 ppb) in PBS.

| Time | Treatment | | | |
|---|---|---|---|---|
| (min) | Control | Citral | Citral + Silver | Silver |
| 1 | ND | 0.06 ± 0.03 | 0.06 ± 0.05 | ND |
| 5 | ND | 1.52† ± 0.19 | 2.25† ± 0.61 | ND |
| 10 | ND | 2.63† ± 0.76 | 4.30†§ ± 0.47 | ND |
| 20 | ND | 3.57† ± 0.35 | >5.28†§ ± 0.40 | ND |
| 30 | 0.05 ± 0.03 | 4.35† ± 0.61 | >5.28† ± 0.34 | 0.01 ± 0.04 |

ND = Not determined
*Inoculated with $1.7 \times 10^7$ CFU/ml
†Reduction was statistically significant (P ≤ 0.05) in comparison to the control (with no antimicrobials)
§Reductions were significantly different (P ≤ 0.05) between citral with and without silver

EXAMPLE 3

Carvacrol Alone or with Silver

Likewise, significant reductions were observed within 5 min of exposure (and each time interval thereafter) with both the carvacrol alone and the carvacrol combined with Ag treatments (Table 2). The carvacrol/Ag combined treatment also yielded greater reductions than carvacrol alone at both 10 and 30 min of exposure.

TABLE 2

Reduction ($\text{Log}_{10}$ ± standard deviation)* in the population of *Escherichia coli* after exposure to 0.02% carvacrol (vol/vol) with and without silver (100 ppb) in PBS.

| Time | Treatment | | | |
|---|---|---|---|---|
| (min) | Control | Carvacrol | Carvacrol + Silver | Silver |
| 5 | ND | 0.35† ± 0.07 | 0.45† ± 0.16 | 0.08 ± 0.12 |
| 10 | ND | 0.50† ± 0.05 | 1.03†§ ± 0.07 | 0.00 ± 0.06 |
| 30 | 0.09 ± 0.04 | 1.44† ± 0.06 | 2.31†§ ± 0.04 | 0.00 ± 0.04 |

ND = Not determined
*Inoculated with $2.9 \times 10^7$ CFU/ml
†Reduction was statistically significant (P ≤ 0.05) in comparison to the control (with no antimicrobials)
§Reductions were significantly different (P ≤ 0.05) between carvacrol with and without silver

EXAMPLE 4

Cinnamaldehyde Alone or with Silver

The reductions observed with cinnamaldehyde (Table 3) were significant within 20 min in comparison to the control. The reduction was more rapid when cinnamaldehyde was combined with silver, with a significant reduction observed within 10 min of exposure. In addition, the cinnamaldehyde/Ag combination had greater reductions (P≤0.05) at both the 20- and 30-min exposure intervals.

TABLE 3

Reduction ($\text{Log}_{10}$ ± standard deviation)* in the population of *Escherichia coli* after exposure to 0.1% cinnamaldehyde (vol/vol) with and without silver (100 ppb) in PBS.

| Time | Treatment | | | |
|---|---|---|---|---|
| (min) | Control | Cinnamaldehyde | Cinnamaldehyde + Silver | Silver |
| 1 | ND | 0.05 ± 0.04 | 0.10 ± 0.08 | ND |
| 5 | ND | 0.18 ± 0.04 | 0.15 ± 0.05 | ND |
| 10 | ND | 0.17 ± 0.07 | 0.54† ± 0.24 | ND |
| 20 | ND | 0.69† ± 0.12 | 1.72†§ ± 0.48 | ND |
| 30 | 0.08 ± 0.04 | 1.79† ± 0.36 | 4.46†§ ± 0.94 | 0.12 ± 0.10 |

ND = Not determined
*Inoculated with $2.1 \times 10^7$ CFU/ml
†Reduction was statistically significant (P ≤ 0.05) in comparison to the control (with no antimicrobials)
§Reductions were significantly different (P ≤ 0.05) between cinnamaldehyde with and without silver

EXAMPLE 5

Allspice Alone or with Silver

No significant reductions were observed with the 0.5% allspice treatment (Table 4). In contrast, a significant reduction of 2.68-$\log_{10}$ was observed after 30 min of exposure when the antimicrobial was combined with Ag.

TABLE 4

Reduction ($\text{Log}_{10}$ ± standard deviation)* in the population of *Escherichia coli* after exposure to 0.5% allspice oil (vol/vol) with and without silver (100 ppb) in PBS.

| Time | Treatment | | | |
|---|---|---|---|---|
| (min) | Control | Allspice Oil | Allspice Oil + Silver | Silver |
| 1 | ND | 0.00 ± 0.16 | 0.04 ± 0.23 | 0.00 ± 0.03 |
| 5 | ND | 0.00 ± 0.05 | 0.00 ± 0.09 | 0.00 ± 0.08 |
| 10 | ND | 0.00 ± 0.17 | 0.12 ± 0.26 | 0.00 ± 0.12 |
| 20 | ND | 0.00 ± 0.08 | 0.03 ± 0.19 | 0.00 ± 0.23 |
| 30 | 0.58 ± 0.34 | 0.55 ± 0.04 | 2.68†§ ± 0.16 | 0.29 ± 0.32 |

ND = Not determined
*Inoculated with $6.6 \times 10^6$ CFU/ml
†Reduction was statistically significant (P ≤ 0.05) in comparison to the control (with no antimicrobials)
§Reductions were significantly different (P ≤ 0.05) between allspice oil with and without silver

EXAMPLE 6

Effect of Different Citral Doses on Bacterial Growth

Table 5 shows the effect of different amounts of citral alone on *E. coli* viability. Viability was measured as described in Example 1.

TABLE 5

Reduction ($Log_{10}$ ± standard deviation)* in the population of *Escherichia coli* after exposure to various concentrations of citral in PBS.

| Time | Citral (vol/vol) | |
|---|---|---|
| (min) | 0.05% | 0.1% |
| 1 | 0.06§ ± 0.03 | 0.23†§ ± 0.11 |
| 5 | 1.52†§ ± 0.19 | 4.13†§ ± 0.54 |
| 10 | 2.63†§ ± 0.76 | >5.53†§ ± 0.00 |
| 20 | 3.57†§ ± 0.35 | >5.53†§ ± 0.00 |
| 30 | 4.35†§ ± 0.61 | >5.53†§ ± 0.00 |

*The initial bacterial inocula ranged from $1.7 \times 10^7$ to $2.5 \times 10^7$ CFU/ml. All experiments were conducted in triplicate.
†The reduction was statistically significant ($P \le 0.05$) in comparison to the control (with no antimicrobial).
§Reductions were significantly different ($P \le 0.05$) between the two different citral concentrations.

EXAMPLE 7

Effect of Different Cinnamaldehyde Doses on Bacterial Growth

Table 6 shows the effect of different amounts of cinnamaldehyde on *E. coli* viability. Viability was measured as described in Example 1.

TABLE 6

Reduction ($Log_{10}$ ± standard deviation)* in the population of *Escherichia coli* after exposure to various concentrations of cinnamaldehyde in PBS.

| Time | Cinnamaldehyde (vol/vol) | |
|---|---|---|
| (min) | 0.1% | 0.2% |
| 1 | 0.05 ± 0.04 | 0.69†§ ± 0.04 |
| 5 | 0.18§ ± 0.04 | 3.01†§ ± 0.40 |
| 10 | 0.17§ ± 0.07 | 5.11†§ ± 0.91 |
| 15 | 0.69†§ ± 0.12 | ND |
| 30 | 1.79†§ ± 0.36 | >5.64†§ ± 0.00 |

ND Not determined.
*The initial bacterial inoculum was $2.1 \times 10^7$ and $2.4 \times 10^7$ CFU/ml for the 0.1% and 0.2% cinnamaldehyde experiments, respectively. The experiments were conducted in triplicate.
†The reduction was statistically significant ($P \le 0.05$) in comparison to the control (with no antimicrobial).
§Reductions were significantly different ($P \le 0.05$) between the two different cinnamaldehyde concentrations.

EXAMPLE 8

Effect of Different Carvacrol Doses on Bacterial Growth

Table 7 shows the effect of different amounts of carvacrol on *E. coli* viability. Viability was measured as described in Example 1.

TABLE 7

Reduction ($Log_{10}$ ± standard deviation)* in the populations of *Escherichia coli* after exposure to various concentrations of carvacrol in PBS.

| Time | Carvacrol (vol/vol) | |
|---|---|---|
| (min) | 0.02% | 0.04% |
| 1 | ND | ND |
| 5 | 0.48†§ ± 0.10 | >5.67†§ ± 0.00 |
| 10 | 0.98†§ ± 0.05 | >5.67†§ ± 0.00 |

TABLE 7-continued

Reduction ($Log_{10}$ ± standard deviation)* in the populations of *Escherichia coli* after exposure to various concentrations of carvacrol in PBS.

| Time | Carvacrol (vol/vol) | |
|---|---|---|
| (min) | 0.02% | 0.04% |
| 20 | ND | ND |
| 30 | 2.27†§ ± 0.22 | >5.67†§ ± 0.00 |

ND Not determined.
*The initial bacterial inoculum was $2.4 \times 10^7$ CFU/ml. The experiment was conducted in triplicate.
†The reduction was statistically significant ($P \le 0.05$) in comparison to the control (with no antimicrobial).
§Reductions were significantly different ($P \le 0.05$) between the two different carvacrol concentrations.

EXAMPLE 9

Effect of Different Allspice Doses on Bacterial Growth

Table 8 shows the effect of different amounts of allspice on *E. coli* viability. Viability was measured as described in Example 1.

TABLE 8

Reduction ($Log_{10}$ ± standard deviation)* in the populations of *Escherichia coli* after exposure to various concentrations of allspice in PBS.

| Time | Allspice Oil (vol/vol) | |
|---|---|---|
| (min) | 0.5% | 1.0% |
| 1 | 0.00§ ± 0.16 | >5.52†§ ± 0.00 |
| 5 | 0.00§ ± 0.05 | >5.52†§ ± 0.00 |
| 10 | 0.00§ ± 0.17 | >5.52†§ ± 0.00 |
| 20 | 0.00§ ± 0.08 | >5.52†§ ± 0.00 |
| 30 | 0.55§ ± 0.04 | >5.52†§ ± 0.00 |

*Inoculated with $6.6 \times 10^6$ CFU/ml and $2.3 \times 10^7$ CFU/ml for the experiment with 0.5% and 1.0% allspice oil, respectively. The experiments were conducted in triplicate.
†Reduction was statistically significant ($P \le 0.05$) in comparison to the control (with no antimicrobial).
§Reductions were significantly different ($P \le 0.05$) between the two different allspice oil concentrations.

EXAMPLE 10

Effect of Different Olive Extract Doses on Bacterial Growth

Table 8 shows the effect of different amounts of olive extract (obtained from CreAgri, Inc. of Hayward, Calif.) on *E. coli* viability. Viability was measured as described in Example 1.

TABLE 9

Reduction ($Log_{10}$ ± standard deviation)* in the populations of *Escherichia coli* after exposure to various concentrations of olive extract in PBS.

| Time | Olive Extract (wt/vol) | |
|---|---|---|
| (min) | 1.0% | 2.5% |
| 15 | 1.02† ± 0.15 | 1.22† ± 0.25 |
| 20 | 2.29† ± 0.11 | 2.24† ± 0.12 |
| 25 | 2.73†§ ± 0.11 | 3.39†§ ± 0.15 |
| 30 | 3.08†§ ± 0.01 | 4.81†§ ± 0.23 |

*Inoculated with $1.5 \times 10^7$ CFU/ml and $1.2 \times 10^7$ CFU/ml for the experiment with 1.0% and 2.5% olive extract, respectively. The experiments were conducted in triplicate.
†Reduction was statistically significant ($P \le 0.05$) in comparison to the control (with no antimicrobial).
§Reductions were significantly different ($P \le 0.05$) between the two different olive extract concentrations.

Table 10 shows the effect of different amounts of olive extract in the presence or absence of silver on *E. coli*. Compositions were prepared, and viability was measured as described in Example 1. As shown in Table 10, although olive extract alone has antimicrobial activity, this effect is reduced in the presence of silver ions. Thus, silver is antagonistic to antimicrobial activity, not synergistic, with olive extract.

TABLE 10

Reduction (Log10 ± standard deviation)* in the population of *Escherichia coli* after exposure to 2.5% olive extract (wt/vol) with and without silver (100 ppb) in PBS.

| Time (min) | Control $Log_{10}$ Reduction ± SD | Olive Extract $Log_{10}$ Reduction ± SD | Olive Extract + Silver $Log_{10}$ Reduction ± SD |
|---|---|---|---|
| 15 | — | $1.22^{\dagger} \pm 0.25$ | $0.83^{\dagger} \pm 0.12$ |
| 20 | — | $2.24^{\dagger\S} \pm 0.12$ | $1.62^{\dagger\S} \pm 0.06$ |
| 25 | — | $3.39^{\dagger\S} \pm 0.15$ | $2.89^{\dagger\S} \pm 0.10$ |
| 30 | $0.00 \pm 0.04$ | $4.81^{\dagger} \pm 0.23$ | $>4.75^{\dagger} \pm 0.63$ |

*Inoculated with $1.2 \times 10^7$ CFU/ml. The experiment was conducted in triplicate.
†Reduction was statistically significant ($P \leq 0.05$) in comparison to the control (with no antimicrobial).
§Reductions were significantly different ($P \leq 0.05$) between the olive extract with or without silver.

REFERENCES

Adams, T. B., Cohen, S. M., Doull, J., Feron, V. J., Goodman, J. I., Marnett, L. J., Munro, I. C., Portoghese, P. S., Smith, R. L., Waddell, W. J. and Wagner, B. M. (2004) The FEMA GRAS assessment of cinnamyl derivatives used as flavor ingredients. *Food Chem Toxicol* 42, 157-185.

Anonymous (1989) In *Hach Water Analysis Handbook* pp. 160-161. Loveland: Hach Company.

Armon, R., Laot, N., Lev, O., Shuval, H. and Fattal, B. (2000) Controlling biofilm formation by hydrogen peroxide and silver combined disinfectant. *Water Sci Technol* 42, 187-192.

Burt, S. (2004) Essential oils: their antibacterial properties and potential applications in foods—A review. *Int J Food Microbiol* 94, 223-253.

Butkus, M. A., Labare, M. P., Starke, J. A., Moon, K. and Talbot, M. (2004) Use of aqueous silver to enhance inactivation of coliphage MS-2 by UV disinfection. *Appl Environ Microbiol* 70, 2848-2853.

Callaway, T. R., Carroll, J. A., Arthington, J. D., Pratt, C., Edrington, T. S., Anderson, R. C., Galyean, M. L., Ricke, S. C., Crandall, P. and Nisbet, D. J. (2008) Citrus products decrease growth of *E. coli* O157: H7 and *Salmonella Typhimurium* in pure culture and in fermentation with mixed ruminal microorganisms in vitro. *Foodborne Pathog Dis* 5, 621-627.

Cox, S. D. and Markham, J. L. (2007) Susceptibility and intrinsic tolerance of *Pseudomonas aeruginosa* to selected plant volatile compounds. *J Appl Microbiol* 103, 930-936.

Didry, N., Dubreuil, L. B. and Pinkas, M. A. (1994) Activity of thymol, carvacrol, cinnamaldehyde and eugenol on oral bacteria. *Pharm Acta Helv* 69, 25-28.

Dillon, V. M. (1999) Natural Anti-Microbial Systems (a) Preservative effects during storage. In *Encyclopedia of Food Microbiology* ed. Robinson, R. K., Batt, C. A. and Patel, P. pp. 1570-1576. Boston: Academic Press.

Friedman, M., Henika, P. R. and Mandrell, R. E. (2002) Bactericidal activities of plant essential oils and some of their isolated constituents against *Campylobacter jejuni*, *Escherichia coli*, *Listeria monocytogenes*, and *Salmonella enterica*. *J Food Protect* 65, 1545-1560.

Gentry, H. and Cope. S. (2005) Using silver to reduce catheter-associated urinary tract infections. *Nurs Stand* 19, 51-54.

Gupta, S. and Ravishankar, S. (2005) A comparison of the antimicrobial activity of garlic, ginger, carrot, and turmeric pastes against *Escherichia coli* O157:H7 in laboratory buffer and ground beef. *Foodborne Pathog Dis* 2, 330-340.

Ibarluzea, J., Moreno, B., Zigorraga, C., Castilla, T., Martinez, M. and Santamaria, J. (1998) Determinants of the microbiological water quality of indoor swimming-pools in relation to disinfection. *Water Res* 32, 865-871.

Kim, H., Shim, J. and Lee, S. (2002) Formation of disinfection by-products in chlorinated swimming pool water. *Chemosphere* 46, 123-130.

Knowles, J. R., Roller, S., Murray, D. B. and Naidu, A. S. (2005) Antimicrobial action of carvacrol at different stages of dual-species biofilm development by *Staphylococcus aureus* and *Salmonella enterica* serovar *Typhimurium*. *Appl Environ Microbiol* 71, 797-803.

Lansdown, A. (2006) Silver in health care: antimicrobial effects and safety in use. *Curr Probl Dermatol* 33, 17-34.

Masahiro, O., Midori, H., Shiro, U. and Toyoshige, E. (2000) Antioxidant activity of eugenol and related monomeric and dimeric compounds. *Chem Pharm Bull* 48, 1467-1469.

Matthews, K. R. (2009) Leafy Vegetables. In *The Produce Contamination Problem: Causes and Solutions* ed. Sapers, G. M., Solomon, E. B. and Matthews, K. R. pp. 165-188. Boston: Academic Press.

Mihara, S. and Shibamoto, T. (1982) Photochemical reactions of eugenol and related compounds: synthesis of new flavor chemicals. *J Agric Food Chem* 30, 1215-1218.

Nannapaneni, R., Muthaiyan, A., Crandall, P. G., Johnson, M. G., O'Bryan, C. A., Chalova, V. I., Callaway, T. R., Carroll, J. A., Arthington, J. D., Nisbet, D. J. and Ricke, S. C. (2008) Antimicrobial activity of commercial citrus-based natural extracts against *Escherichia coli* O157:H7 isolates and mutant strains. *Foodborne Pathog Dis* 5, 695-699.

Olasupo, N. A., Fitzgerald, D. J., Gasson, M. J. and Narbad, A. (2003) Activity of natural antimicrobial compounds against *Escherichia coli* and *Salmonella enterica* serovar *Typhimurium*. *Lett Appl Microbiol* 37, 448-451.

Peñalver, P., Huerta, B., Borge, C., Astorga, R., Romero, R. and Perea, A. (2005) Antimicrobial activity of five essential oils against origin strains of the Enterobacteriaceae family. *APMIS* 113, 1-6.

Privett, B. J., Deupree, S. M., Backlund, C. J., Rao, K. S., Johnson, C. B., Coneski, P. N. and Schoenfisch, M. H. (2010) Synergy of nitric oxide and silver sulfadiazine against Gram-negative, Gram-positive, and antibiotic-resistant pathogens. *Mol Pharm* 7, 2289-2296.

Ravishankar, S., Zhu, L., Joens, L. and Friedman, M. (2008) Plant-derived compounds inactivate antibiotic resistant *Campylobacter jejuni* strains. *J Food Protect* 71, 1145-1149.

Ravishankar, S., Zhu, L., Olsen, C. W., McHugh, T. H. and Friedman, M. (2009) Edible apple film wraps containing plant antimicrobials inactivate foodborne pathogens in meat and poultry products. *J Food Sci* 74, M440-M445.

Ravishankar, S., Zhu, L., Reyna-Granados, J., Law, B., Joens, L. and Friedman, M. (2010) Carvacrol and cinnamaldehyde inactivate antibiotic-resistant *Salmonella enterica* in buffer and on celery and oysters. *J Food Protect* 73, 234-240.

Ress, N. B., Hailey, J. R., Maronpot, R. R., Bucher, J. R., Travlos, G. S., Haseman, J. K., Orzech, D. P., Johnson, J. D. and Hejtmancik, M. R. (2003) Toxicology and Carcinogenesis studies of microencapsulated citral in rats and mice. *Toxicol Sci* 71, 198-206.

Silver, S. (2003) Bacterial silver resistance: Molecular biology and uses and misuses of silver compounds. *FEMS Microbiol Rev* 27, 341-353.

Silvestry-Rodriguez, N., Bright, K. R., Uhlmann, D. R., Slack, D. C. and Gerba, C. P. (2007a) Inactivation of *Pseudomonas aeruginosa* and *Aeromonas hydrophila* by silver in tap water. *J Environ Sci Health, Part A Tox Hazard Subst Environ Eng* 42, 1579-1584.

Silvestry-Rodriguez, N., Sicairos-Ruelas, E. E., Gerba, C. P. and Bright, K. R. (2007b) Silver as a disinfectant. *Rev Environ Contam Toxicol* 191, 23-45.

Singh, N., Singh, R. K. and Bhunia, A. K. (2003) Sequential disinfection of *Escherichia coli* O157:H7 inoculated alfalfa seeds before and during sprouting using aqueous chlorine dioxide, ozonated water, and thyme essential oil. *Lebensm Wiss U.-Technol* 36, 235-243.

Somolinos, M., Garcia, D., Condon, S., Mackey, B. and Pagan, R. (2010) Inactivation of *Escherichia coli* by citral. *J Appl Microbiol* 108, 1928-1939.

Uhart, M., Maks, N. and Ravishankar, S. (2006) Effect of spices on growth and survival of *Salmonella Typhimurium* DT 104 in ground beef stored at 4 and 8° C. *J Food Saf* 26, 115-125.

Yahya, M. T., Straub, T. M. and Gerba, C. P. (1992) Inactivation of coliphage MS-2 and poliovirus by copper, silver and chlorine. *Can J Microbiol* 38, 430-435.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. An antimicrobial composition, comprising:
   one or more of about 0.05% citral (vol/vol), about 0.1% cinnamaldehyde (vol/vol), about 0.02% carvacrol (vol/vol), and about 0.5% allspice (vol/vol); and
   silver ions at a concentration of about 100 parts per billion (ppb),
   wherein the combination of the one or more of citral, cinnamaldehyde, carvacrol, and allspice; and silver ions exhibits antimicrobial synergy.

2. The antimicrobial composition of claim 1, wherein the antimicrobial composition comprises about 0.05% citral (vol/vol) and silver ions at a concentration of about 100 ppb.

3. The antimicrobial composition of claim 1, wherein the antimicrobial composition comprises about 0.1% about cinnamaldehyde (vol/vol) and silver ions at a concentration of about 100 ppb.

4. The antimicrobial composition of claim 1, wherein the antimicrobial composition comprises about 0.02% carvacrol (vol/vol) and silver ions at a concentration of about 100 ppb.

5. The antimicrobial composition of claim 1, wherein the antimicrobial composition comprises about 0.5% allspice (vol/vol) and silver ions at a concentration of about 100 ppb.

6. The antimicrobial composition of claim 1, wherein the composition further comprises water.

7. The antimicrobial composition of claim 1, wherein the remainder of the composition comprises water.

8. The antimicrobial composition of claim 1, wherein the composition further comprises one or more solvents, surfactants, cosurfactants, chelating agents, buffers, thickeners, dyes, colorants, biocides, fragrances, defoamers, and/or acids.

9. A solid support comprising the antimicrobial composition of claim 1.

10. The solid support of claim 9, wherein the solid support comprises a layer of absorbent or adsorbent material.

11. A method of killing a microorganism, comprising:
    contacting the microorganism with the antimicrobial composition of claim 1.

12. The method of claim 11, wherein the microorganism is a bacterium, bacterial spore, helminth, protozoan, fungus, or virus.

13. The method of claim 12, wherein the bacterium is *Escherichia coli*.

14. The method of claim 11, wherein the microorganism is present on a hard surface.

15. The method of claim 11, wherein the microorganism is present on a produce item.

16. The method of claim 11, wherein the microorganism is killed within 10 minutes of contacting with the antimicrobial composition.

17. The method of claim 11, wherein the method reduces a number of viable microorganisms by at least $5\text{-log}_{10}$ within 10 minutes of exposure.

18. The method of claim 11, wherein the method reduces a number of viable microorganisms by at least 10-fold more within 1 to 30 minutes of exposure as compared to contacting the microorganisms with citral, cinnamaldehyde, carvacrol, or allspice without silver.

19. The method of claim 11, wherein the microorganism is present on a meat product, and the method further comprising rinsing the meat product after it has been contacted with the antimicrobial composition.

20. The antimicrobial composition of claim 1, wherein the allspice comprises an allspice oil.

* * * * *